United States Patent
Deane et al.

(10) Patent No.: US 10,376,349 B2
(45) Date of Patent: Aug. 13, 2019

(54) BRUSH HEAD ASSEMBLY

(71) Applicant: KONINKLIJKE PHILIPS N.V., Eindhoven (NL)

(72) Inventors: Steven Charles Deane, Cambridge (GB); Steven Ernest Franklin, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 70 days.

(21) Appl. No.: 15/573,319

(22) PCT Filed: May 11, 2016

(86) PCT No.: PCT/IB2016/052691
§ 371 (c)(1),
(2) Date: Nov. 10, 2017

(87) PCT Pub. No.: WO2016/181319
PCT Pub. Date: Nov. 17, 2016

(65) Prior Publication Data
US 2018/0132989 A1    May 17, 2018

Related U.S. Application Data

(60) Provisional application No. 62/161,367, filed on May 14, 2015.

(51) Int. Cl.
| A46B 3/04 | (2006.01) |
| A46B 3/20 | (2006.01) |
| A46B 7/06 | (2006.01) |
| A46B 9/10 | (2006.01) |
| A61C 17/34 | (2006.01) |
| A61C 17/22 | (2006.01) |
(Continued)

(52) U.S. Cl.
CPC .............. *A61C 17/222* (2013.01); *A46B 3/04* (2013.01); *A46B 3/20* (2013.01); *A46B 7/06* (2013.01); *A46B 9/04* (2013.01); *A46D 3/00* (2013.01); *A61C 17/3409* (2013.01); *A46B 9/10* (2013.01)

(58) Field of Classification Search
CPC .... A46B 3/04; A46B 3/20; A46B 7/06; A46B 9/10; A61C 17/3409; A46D 3/00
See application file for complete search history.

(56) References Cited

U.S. PATENT DOCUMENTS

| 5,474,366 A | 12/1995 | Zahoransky et al. |
| 5,802,656 A | 9/1998 | Dawson et al. |
| 5,970,564 A | 10/1999 | Inns et al. |
(Continued)

FOREIGN PATENT DOCUMENTS

| CN | 104287857 A | 1/2015 |
| DE | 10 2005 009 958 A1 * | 1/2007 |
(Continued)

*Primary Examiner* — Randall E Chin

(57) ABSTRACT

A brush head assembly (100) comprising a sandwich assembly (200) comprising a flexible matrix (30″) positioned between two layers of stiff or stiffer material (220), a plurality of bristle tufts (21), each of which comprises a plurality of bristle strands, each bristle tuft having a proximal end (23) and a free end (25), a bristle tuft retention element (250) for each bristle tuft (21), the bristle tuft retention elements (250) connecting the proximal end of the bristle tufts (21) to the sandwich assembly.

14 Claims, 9 Drawing Sheets

(51) Int. Cl.
*A46B 9/04* (2006.01)
*A46D 3/00* (2006.01)

(56) References Cited

U.S. PATENT DOCUMENTS

| | | | |
|---|---|---|---|
| 6,036,277 A * | 3/2000 | Weihrauch | A46B 3/20 |
| | | | 15/186 |
| 6,088,870 A | 7/2000 | Holbein | |
| 6,406,099 B2 | 6/2002 | Boucherie | |
| 7,281,768 B2 | 10/2007 | Sato et al. | |
| 7,600,288 B1 | 10/2009 | Givonetti | |
| 7,743,452 B1 * | 6/2010 | Tcholakov | A46B 7/06 |
| | | | 15/167.1 |
| 7,836,537 B1 | 11/2010 | Kumar | |
| 7,992,247 B2 | 8/2011 | Pfenniger et al. | |
| 8,069,524 B2 | 12/2011 | Kraemer | |
| 8,099,819 B2 | 1/2012 | Kraemer | |
| 8,132,284 B1 * | 3/2012 | Kraemer | A46B 3/20 |
| | | | 15/167.1 |
| 2001/0024060 A1 | 9/2001 | Boucherie | |
| 2001/0038237 A1 | 11/2001 | Boucherie | |
| 2003/0041402 A1 | 3/2003 | Stein et al. | |
| 2005/0015909 A1 * | 1/2005 | Spitale | A46B 3/20 |
| | | | 15/191.1 |
| 2007/0006410 A1 | 1/2007 | Kraemer | |
| 2007/0271717 A1 | 11/2007 | Clos | |
| 2008/0168613 A1 | 7/2008 | Kraemer | |
| 2012/0204370 A1 * | 8/2012 | Crossman | A46B 7/06 |
| | | | 15/167.1 |
| 2012/0233790 A1 | 9/2012 | Uchida et al. | |
| 2014/0232173 A1 | 8/2014 | Birk et al. | |
| 2014/0373294 A1 | 12/2014 | Schuster | |

FOREIGN PATENT DOCUMENTS

| | | |
|---|---|---|
| EP | 1593321 A1 | 11/2005 |
| EP | 2708155 A1 | 3/2014 |
| JP | H07265127 A | 10/1995 |
| WO | 2004080238 A1 | 9/2004 |
| WO | 2006109077 A1 | 10/2006 |

* cited by examiner

BRUSH HEAD ASSEMBLY

CROSS-REFERENCE TO PRIOR APPLICATIONS

This application is the U.S. National Phase application under 35 U.S.C. § 371 of International Application No. PCT/IB2016/052691, filed on May 11, 2016, which claims the benefit of U.S. Provisional Patent Application No. 62/161,367 filed on May 14, 2015. These applications are hereby incorporated by reference herein.

FIELD OF THE INVENTION

The present disclosure is directed generally to a brush head assembly, for example a brush head assembly for use with a personal care appliance, such as a power toothbrush.

BACKGROUND

Periodontal diseases are thought to be infectious diseases caused by bacteria present in dental plaques. Removal of dental plaques is highly important for the health of oral cavities. Tooth brushing is a highly effective method to remove dental plaque from the teeth. Power toothbrushes can enhance the removal of dental plaque. Such power toothbrushes have a set of bristles attached to a brush head which is moved by a driver that causes the bristles to scrub dental surfaces.

Bristles need to be secured in a brush head in a method that keeps them secured in the brush head during use, but provides flexibility for the bristles while brushing. Anchor-free tufting of bristles provides greater flexibility. However, with anchor-free tufting, the bristle tuft can be or become loose within the brush head and the bristles might not always be positioned at an angle optimal for brushing. This is especially true with the motion of power toothbrushes. Further, the process of organizing the bristles into tufts and then forming the brush head material can be time-consuming and expensive.

In addition, the teeth and gums are a complex shaped surface, with significant curvature and variation between individuals. Cleaning plaque efficiently from all surfaces is the goal of oral care, but is particularly difficult from the regions where teeth meet, or along the gum line. Achieving good cleaning is a key goal of toothbrush head design. In certain examples some groups of bristles in the brush head are longer than the rest of the bristles, so that they can access the interproximal spaces better. In the Philips Adaptiveclean brush head, groups of bristles are mounted in an elastomer to provide an ability to flex more than traditional brush heads, to allow adaptation to the underlying contours in the mouth.

A further consideration is the length of the bristles. In particular, the bristle length in a toothbrush is a compromise; longer bristles allow more splaying over the topography of the teeth. However longer bristles also make the brush head bulkier and harder to manoeuvre in the mouth, resulting in difficulty accessing some areas of the teeth. The bristle length chosen is a compromise of these and other factors.

Bristles clean effectively over a certain range of contact forces. If the bristles do not make contact with the surface of the teeth (i.e. the contact force is too low), then cleaning efficiency is far lower than if in contact. A contact force that is too low will not penetrate the plaque, while a contact force that is too high may result in the bristles becoming stationary on the surface of the tooth or gum due to friction forces between the end of the bristles and the tooth or gums exceeding lateral forces (i.e. forces that aim to move the bristles across the teeth), which also leads to ineffective plaque removal. The properties of the elastomer in the Philips Adaptiveclean brush head is a necessary compromise between being soft enough to provide some conformation to the tooth surface, while being firm enough to transmit the lateral forces needed to sweep the bristles.

Accordingly, there is a need in the art for improved brush head assemblies, and methods of their manufacture, that increase the retention of the bristles on the brush head while still providing for flexibility of the bristles during use, and therefore improving oral care.

As noted above there is also, or alternatively, a need in the art for brush head assemblies, and methods of their manufacture, that improve the conformity of the brush head to the tooth and/or gum topography while improving the transmission of lateral forces needed to sweep the bristles.

SUMMARY OF THE INVENTION

Some embodiments of the present disclosure are directed to inventive brush heads with bristle tufts permanently retained within a sandwich of flexible material between two layers of stiffer material, or a shear-thickening (non-Newtonian) material, either alone or in conjunction with one or more layers of stiffer material. In some arrangements, the bristle tufts are held in a retention element, such as a ring, sleeve, anchor or webbing. In some arrangements, an additional backing material is used, either alone, or encapsulating the various other layers, or parts thereof. In some embodiments and implementations, a neck or platen is embedded within the backing material, resulting in a completed brush head. Using the various embodiments and implementations herein, cost-effective and efficient production of brush heads with secured bristle tufts is substantially improved.

The brush heads disclosed and described herein can be used with any manual or power toothbrush device. One example of a power toothbrush device that the brush head can be used with Sonicare® devices available from Koninklijke Philips Electronics N.V. This oral care device is based upon an actuator with a reciprocating brush head including bristles to provide an effective cleaning of a user's teeth.

In accordance with a first specific aspect, there is provided a brush head assembly comprising a sandwich assembly comprising a flexible matrix positioned between two layers of stiff or stiffer material, a plurality of bristle tufts, each of which comprises a plurality of bristle strands, each bristle tuft having a proximal end and a free end, a bristle tuft retention element for each bristle tuft, the bristle tuft retention elements connecting the proximal end of the bristle tufts to the sandwich assembly.

According to a second specific aspect, there is provided a method of manufacturing a brush head assembly for use with a personal care appliance, the method comprising providing a plurality of bristle tufts, each of which comprising a plurality of bristle strands, each bristle tuft having a proximal end and a free end; providing a bristle tuft retention element for each bristle tuft; providing a sandwich assembly comprising a flexible matrix positioned between two layers of stiff or stiffer material; and connecting the bristle tuft retention elements to the sandwich assembly.

According to a third specific aspect, there is provided a brush head assembly comprising a hard platen; a plurality of bristle tufts, each of which comprises a plurality of bristle strands, each bristle tuft having a proximal end and a free end; and a flexible matrix at least partially comprised of a shear-thickening material for coupling the plurality of bristle tufts to the hard platen, wherein the flexible matrix is arranged such that there is shear-thickening material between the proximal ends of the plurality of bristle tufts and the hard platen.

According to a fourth specific aspect, there is provided a method of manufacturing a brush head assembly for use with a personal care appliance, the method comprising providing a hard platen and a plurality of bristle tufts, each of which comprising a plurality of bristle strands, each bristle tuft having a proximal end and a free end; and coupling the plurality of bristle tufts to the hard platen using a flexible matrix at least partially comprised of a shear-thickening material, wherein the flexible matrix is arranged such that there is shear-thickening material between the proximal ends of the plurality of bristle tufts and the hard platen.

BRIEF DESCRIPTION OF THE DRAWINGS

The embodiments of the present disclosure may take form in various components and arrangements of components, and in various steps and arrangements of steps. Accordingly, the drawings are for purposes of illustrating the various embodiments and are not to be construed as limiting the embodiments. In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

Figure 1:
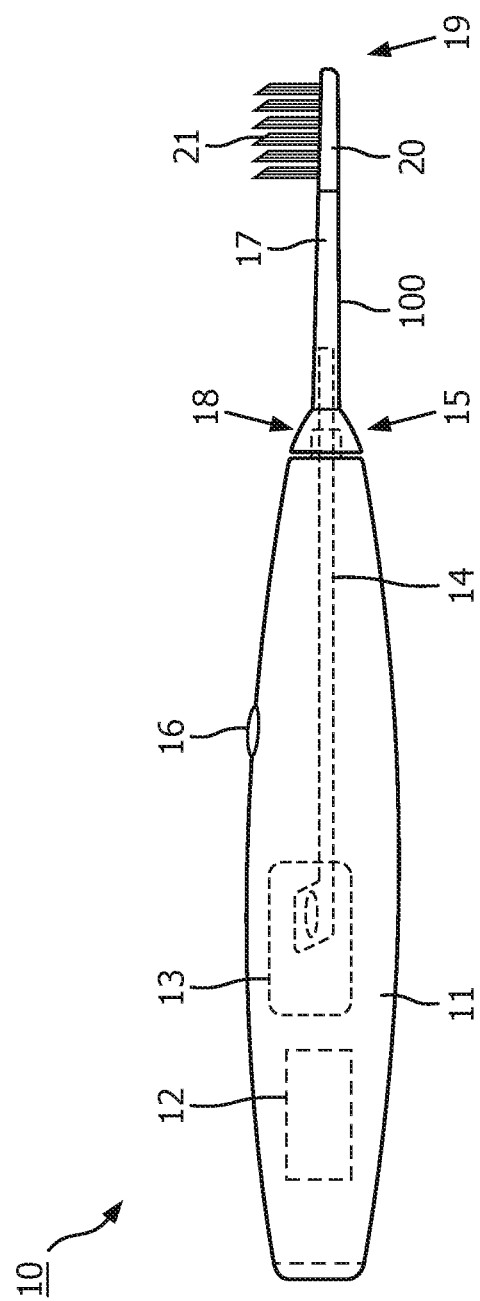
FIG. 1 is a schematic view of a personal care appliance, such as a power toothbrush.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

With reference now to FIG. 1, there is shown a schematic view of a personal care appliance 10 of the present disclosure. According to the embodiments of the present disclosure, the personal care appliance comprises a handle 11, a motor controller 12 (that is located in the handle 11), and a brush head assembly 100. In one embodiment, the brush head assembly 100 comprises or is a replaceable attachment, i.e. the brush head assembly 100 can be removed from the personal care appliance 10 and replaced by another brush head assembly 100. The personal care appliance 10 preferably comprises or is a power toothbrush. The handle 11 includes a drive train 13 and a drive shaft 14. The drive shaft 14 extends from a distal end 15 of the handle 11, and into the brush head assembly 100 when a brush head assembly 100 is attached to the handle 11.

Motor controller 12 (i.e., control electronics) comprises any suitable controller, microcontroller, processor, power source and/or other electronics to provide power and control signals for implementing the various functions, or any combination thereof, as discussed further herein. In addition, the personal care appliance 10 can further comprise an activation button 16 (or an equivalent mechanism) that is operable between at least (i) an OFF state and (ii) at least one activation ON state. The at least one activation ON state can comprise one or more operation states for implementing various care routines and/or operations with the personal care appliance 10.

In embodiments, motor controller 12 can be configured for controlling an operation or operations of the drive train 13 to produce a mechanical stimulus. The mechanical stimulus can comprise vibrations or other movements at a high frequency, for example, a frequency greater than 50 Hz, and for example a frequency in the range of 250-300 Hz.

The brush head assembly 100 has a neck or body 17 with a principal axis extending between a proximal end 18 and a distal end 19 of the brush head assembly 100. The proximal end 18 couples, via a press fit or other suitable coupling mechanism (which is not shown in FIG. 1), to the portion of drive shaft 14 extending from the distal end 15 of the handle 11. The distal end 19 of the brush head assembly 100 can include a head portion 20 with a plurality of bristle tufts 21 comprising a plurality of bristles or bristle strands, configured according to the requirements of a specific application of the brush head assembly 100. The bristle tufts 21 can be arranged in one or more rows or columns in the head portion 20 as required for the specific application of the brush head assembly 100. The bristle strands in the bristle tufts 21 can be formed from any suitable material, for example nylon.

In operation, responsive to the motor controller 12 operating to control an operation of the drive train 13 to produce a mechanical stimulus, the brush head assembly 100 implements a cleaning motion.

As noted above, bristles clean effectively over a certain range of contact forces. If the bristles do not make contact with the surface of the teeth (i.e. the contact force is too low), then cleaning efficiency is far lower than if in contact. A contact force that is too low will not penetrate the plaque, while a contact force that is too high may result in the bristles becoming stationary on the surface of the tooth or gum due to friction forces between the end of the bristles and the tooth or gums exceeding lateral forces (i.e. forces that aim to move the bristles across the teeth), which also leads to ineffective plaque removal. The embodiments of the present disclosure thus aim to improve the conformity of the bristles to the tooth and/or gum topography while improving the transmission of lateral forces needed to sweep the bristles across the tooth and/or gum.

Thus the present disclosure describes various embodiments of a brush head assembly 100 with bristle tufts 21 retained within a flexible matrix comprising a flexible material or shear-thickening (non-Newtonian) material, or bristle tufts 21 retained within or interconnected via a sandwich of flexible material between two layers of stiff or stiffer material. More generally, Applicants have recognized and appreciated that it would be beneficial to provide a brush head assembly 100 formed from or comprising a flexible material to provide movement while improving bristle retention, and/or improve conformity to the tooth and/or gum topography while providing for the transmission of lateral forces needed to sweep the bristles. For example, bristle tuft and platen placement can restrict or enhance movement of a flexible or shear-thickening material, which can be beneficial to a brush head's function, especially in powered toothbrush devices.

In view of the foregoing, various embodiments and implementations are directed to a brush head assembly 100 in which a bristle tuft 21 is affixed to or within a flexible material without a retention element such as a ring, sleeve, anchor, or webbing. Alternatively, the bristle tuft 21 is affixed within a retention element, such as a ring, sleeve, anchor or webbing. In some arrangements, a hard platen is also provided, and the components are embedded at least partially within a flexible matrix that at least partially comprises a flexible material or shear-thickening (non-Newtonian) material. In some arrangements, a hard platen is also provided, and the components are retained within, or connected to, a flexible material which may be layered between two layers of harder material.

Figure 2A:
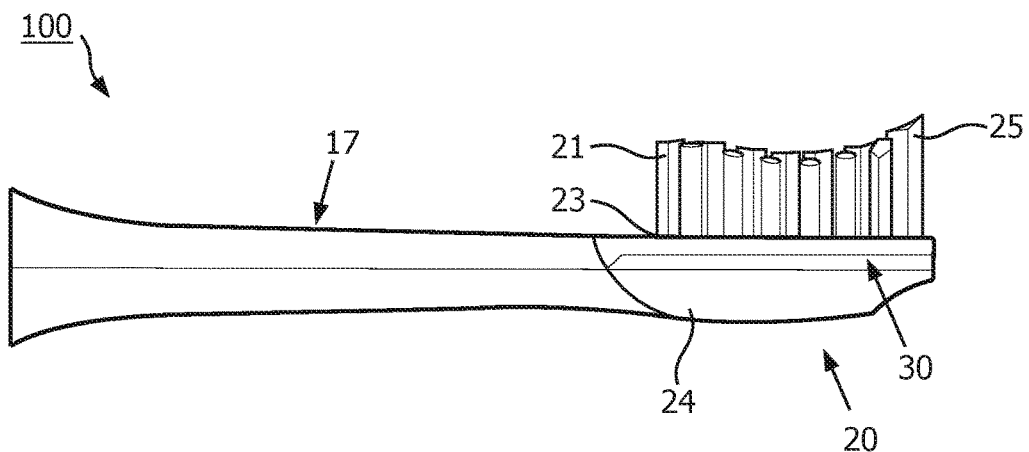
FIG. 2A is a schematic representation of a side view of a brush head assembly in accordance with an embodiment.
Figure 2B:
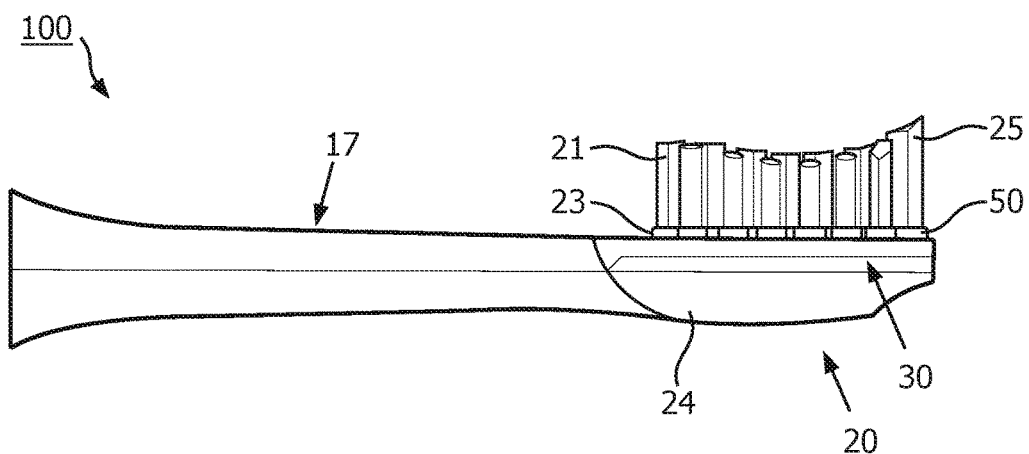
FIG. 2B is a schematic representation of a side view of a brush head assembly in accordance with an embodiment.

Referring to FIGS. 2A and 2B, a schematic representation of a brush head assembly 100 is provided. The brush head includes a body or neck 17, which can be coupled to any manual brush shaft, or, more preferably, to any actuator and drive shaft 14 (not shown) made or suitable for oral care devices now known or to be developed. The brush head assembly 100 includes a plurality of bristle tufts 21, each of which comprises a plurality of bristles or bristle strands. It will be appreciated that the length and/or profile of the bristles in the bristle tufts 21 shown in FIGS. 2A and 2B is merely exemplary, and the bristles can have alternative lengths and/or profile as required for the specific application. According to an embodiment, the bristles in the bristle tufts 21 are composed of nylon, or another suitable material. Each bristle tuft includes a proximal end 23 and a free end 25. The proximal end 23 of the bristle tuft 21 is the end retained, held or otherwise fixed in or to the head portion 20. The free end 25 of the bristle tuft 21 is free to move relative to the head portion 20 to effect the cleaning action on the teeth and/or gums. The neck or body 17 comprises a hard platen 24 to which, in some arrangements, the bristle tufts 21 can be directly or indirectly attached. In some arrangements, as shown in FIG. 2B, a bristle tuft retention element 50 is used to hold the bristle tufts 21.

In some arrangements, which are described further below with reference to FIGS. 3A-3E, the proximal end 23 of each bristle tuft 21, the retention element 50 (if used), and the hard platen 24 portion of the neck 17, if used, are retained within, affixed to, encompassed by or otherwise in contact with a flexible matrix 30, which is preferably made of or at least partially comprises a shear-thickening material, to form the head portion 20.

In other arrangements, which are described further below with reference to FIGS. 5A-5C, FIG. 6 and FIGS. 7A-7B, the retention elements 50 can be coupled or fixed together using a sandwich made of a stiffer material with a flexible material between the stiffer material to form the head portion 20 of the brush head assembly 100.

It will be appreciated that, although flexible matrix 30 is shown in FIG. 2A and FIG. 2B, in some arrangements the flexible matrix 30 may be interior to the head portion 20 and not visible to a user of the brush head assembly 100.

As noted above, during use of a brush head assembly 100, forces are exerted on the bristles that can result in the bristles being removed or expelled from the bristle tuft 21. Accordingly, it is desirable to improve retention of bristles and bristle tufts within the brush head, including within the flexible matrix. Also as noted above, it is also or alternatively desirable to improve conformity of the bristles to the tooth and/or gum topography while providing for the transmission of lateral forces needed to sweep the bristles.

FIGS. 3A-3E illustrate brush head assemblies 100 according to a first set of embodiments in which a flexible matrix 30' that at least partially comprises a shear-thickening material is provided for coupling the plurality of bristle tufts 21 to the hard platen 24. In these embodiments, the flexible matrix 30' is arranged such that there is shear-thickening material between the proximal ends 23 of the plurality of bristle tufts 21 and the hard platen 24.

A shear-thickening material is also known as a dilatant material, or a strain rate dependent material. A dilatant is a Non-Newtonian fluid where the shear viscosity or stiffness increases with applied shear stress. Thus, a shear-thickening material exhibits different levels of stiffness depending on the frequency of motion of the material.

Dilatant materials are typically composed of stabilised suspensions of fine particles, often silica, combined with various long chain polymers to give the desired properties. They may also be incorporated into solids, by being contained in e.g. a cellular foam matrix. The behavior of the dilatant material (e.g. the magnitude of the change in stiffness, the frequency/ies of motion at which the change in stiffness occurs) can be controlled by factors such as particle size, shape and distribution. In some embodiments the dilatant material can be in the form of a foam or polymer that is soft (i.e. deformable). In specific embodiments, the dilatant material can comprise, or be, the material known as the Dow Corning® 3179 Dilatant Compound (http://www.dow-corning.com/applications/search/products/details.aspx?prod=01512137&type=PROD). In specific embodiments, the dilatant material can comprise Dow Corning® 3179 Dilatant Compound in combination with a regular (i.e. non-dilatant) polymer. In another embodiment, the dilatant material can be the material known as D3O.

In some embodiments, in view of the flexibility of certain types of dilatant material at low strain rates (e.g. when the brush head assembly 100 is not being used), to improve the retention of the bristles or bristle tufts 21 in the head portion 20, the flexible matrix 30' can comprise the dilatant material in combination with one or more other, e.g. harder or stiffer, materials to form a composite structure, in or to which the bristles can be attached.

Figure 3A:
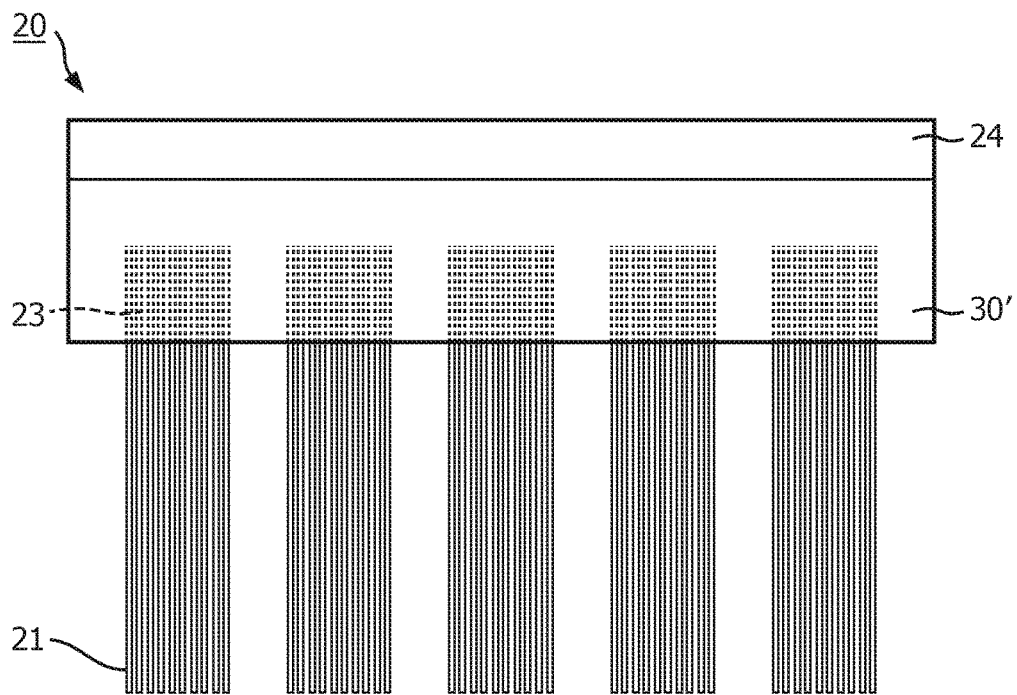
FIG. 3A is a schematic representation of a portion of a brush head assembly in accordance with an embodiment.

FIG. 3A shows one embodiment of a head portion 20 of a brush head designed to improve retention of bristles and bristle tufts 21 and/or improve conformity to the tooth and/or gum topography while providing for the transmission of lateral forces needed to sweep the bristles across the tooth. The head portion 20 comprises a plurality of bristle tufts 21 located within the flexible matrix 30' that at least partially comprises a shear-thickening (non-Newtonian fluid) material. In this embodiment the flexible matrix 30' encompasses the proximal end 23 of the bristle tufts 23, and thus a retention element 50 such as a ring, sleeve, anchor, or webbing is not required to retain the bristle tufts 21 in place. The shear thickening material, or more generally the material of the flexible matrix 30' can be molded over or around the proximal ends 23 of the bristle tufts 21 and the platen 24 and allowed to cure to form the flexible matrix 30' within which the bristle tufts 21 are retained. The flexible matrix 30' can be bonded to at least a portion of the hard platen 24. Optionally, the flexible matrix 30' can be bonded to a surface of the platen 24. Optionally the flexible matrix 30' can also or alternatively be bonded to the proximal end 23 of the bristle tufts 21.

Preferably, the flexible matrix 30', the bristle tufts 21 and the platen 24 are arranged such that there is shear-thickening material (flexible matrix material) between the proximal ends 23 of the plurality of bristle tufts 21 and the hard platen 24. This arrangement enables vertical movement or displacement of the bristle tufts 21 with respect to the platen 24, either as a group or individually, as the brush head assembly 100 is moved across the surface of a tooth and/or the gums. It will be appreciated that vertical movement of the bristle tufts 21 refers to movement in a direction generally parallel to the axis of the bristle tufts 21 (i.e. movement in a direction that is generally perpendicular to the plane of the platen 24.

The distance between the platen 24 and the proximal end of the bristle tufts 21 can be of the order of a few millimetres, e.g. 1 mm-6 mm, and preferably around 4 mm, as these distances cover the typical variation in topology of the tooth and gums.

Thus, the use of shear-thickening materials in or for the flexible matrix 30' in the head portion 20 of the brush head assembly 100 enables the bristles/bristle tufts to better conform to the shape of the teeth and/or gums (such as at low strain rates, on the order of 0.1-2 Hz), and to be far stiffer at higher frequencies (e.g. greater than 50 Hz, and e.g. in the range 250-300 Hz, such as the frequencies at which a personal care appliance can operate) to transmit effectively the lateral forces used for sweeping the bristles across the teeth and/or gums. This means that the shear-thickening material can be flexible in the vertical direction to the low frequency forces resulting from changes in the topology of the tooth and/or gums, and/or stiff to the high frequency lateral forces used for sweeping the bristles across the tooth communicated to the brush head assembly 100 by the drive shaft 14.

Figure 3B:
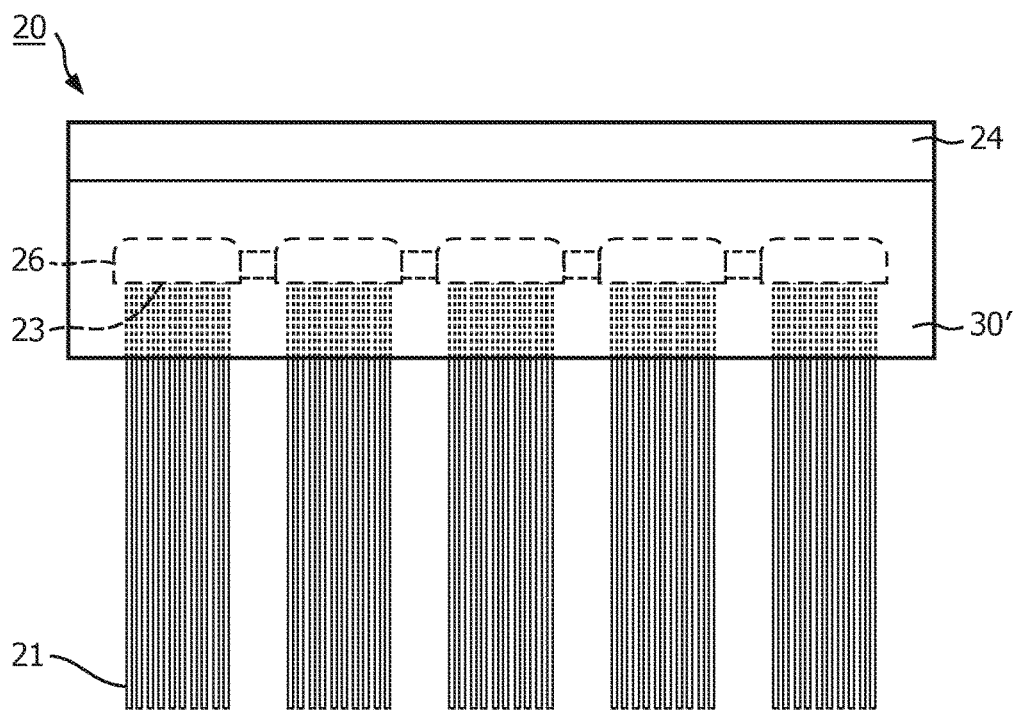
FIG. 3B is a schematic representation of a portion of a brush head assembly in accordance with an embodiment.

FIG. 3B shows another embodiment of a head portion 20 of a brush head designed to improve retention of bristles and bristle tufts 21 within the flexible matrix 30' that at least partially comprises a shear-thickening (non-Newtonian fluid) material. The embodiment in FIG. 3B corresponds to that shown in FIG. 3A, except that the proximal ends 23 of the bristle strands in the bristle tufts 21 have been melted or otherwise processed or formed into proximal end portions 26 that will help to better secure the bristle tufts 21 in the flexible matrix 30'. In particular, the proximal end portions 26 are encompassed by the flexible matrix 30'.

The shear thickening material (or more generally the flexible matrix 30' can be formed or molded over or around at least a portion of the proximal end portions 26, the proximal ends 23 of the bristle tufts 21 and allowed to cure to form the flexible matrix 30' within which the bristle tufts 21 are retained.

Figure 3C:
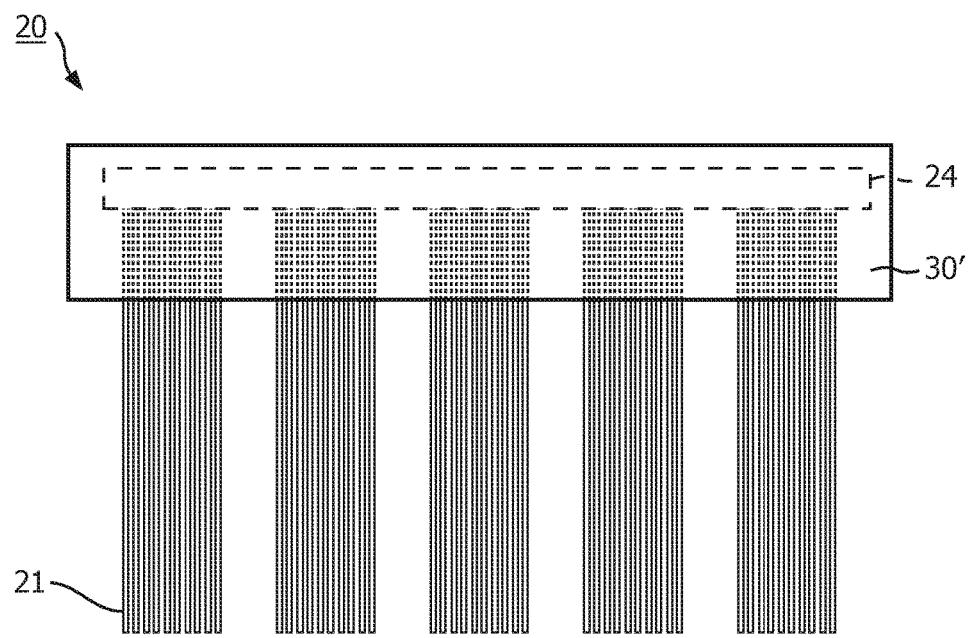
FIG. 3C is a schematic representation of portion of a brush head assembly in accordance with an embodiment.

FIG. 3C shows another embodiment of a head portion 20 designed to improve retention of bristles and bristle tufts 21 within the flexible matrix 30'. The embodiment in FIG. 3C corresponds to that shown in FIG. 3A, except that bristle tufts 21 are attached directly to the platen 24. In particular, the bristle tufts 21 can be melted or dissolved directly into the hard platen 24, or the bristle tufts 21 can be inserted into bristle tuft holes (not shown) in the hard platen 24. The bristles can be free within the bristle tuft holes, or can be melted or fused into the bristle tuft holes, or can be molded in place with an additional securing component. In this embodiment, the shear-thickening material (flexible matrix 30') completely encompasses the platen 24, although this is not required in all implementations. Thus, the flexible matrix 30' can be molded over or around the hard platen 24 and around the proximal ends 23 of the bristle tufts 21 to retain the bristle tufts 21. The bristle tufts 21 can be melted or dissolved directly into the hard platen 24 by designing the bristle tufts and hard platen 24 with specific structural characteristics and melting temperatures.

Figure 3D:
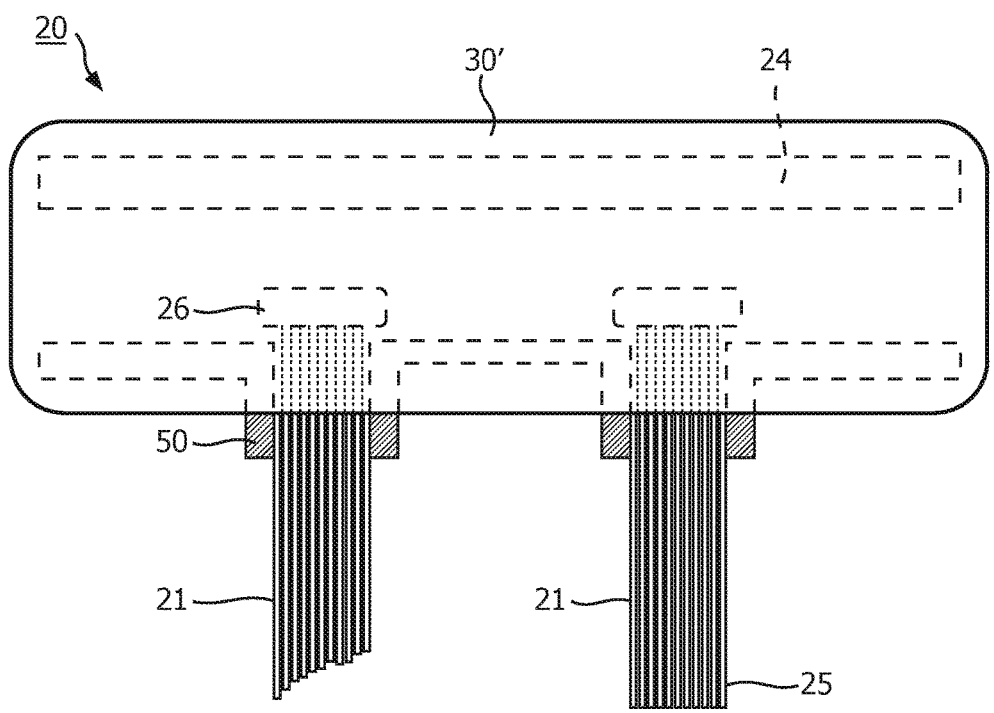
FIG. 3D is a schematic representation of a portion of a brush head assembly in accordance with an embodiment.

FIG. 3D shows another embodiment of a head portion 20 of a brush head assembly 100 designed to improve retention of bristles and bristle tufts 21 within the flexible matrix 30'. This embodiment is similar to the embodiment shown in FIG. 3B and the proximal ends 23 of the bristle tufts 21 can be melted or otherwise processed to form respective proximal end portions 26 that will help to better secure the bristle tufts 21 in the flexible matrix 30', and the platen 24 is fully encompassed by the flexible matrix 30', as in the embodiment of FIG. 3C. This embodiment also includes a retention element 50 which is used to further secure the bristle tufts 21 in the flexible matrix 30'. The shear thickening material (or more generally the flexible matrix material) can be molded over or around the proximal end portions 26, the proximal ends 23 of the bristle tufts 21, at least a portion of the retention element 50, and the platen 24 and allowed to cure to form the flexible matrix 30' within which the bristle tufts 21 are retained. Alternatively, the tufts 21 can be bonded to the retention element 50 rather than being retained by the flexible matrix 30' itself. In the arrangement shown in FIG. 3D, a portion of the retention element 50 is embedded in the flexible matrix 30' with the distal portion of the retention element 50 protruding from the flexible matrix 30' such as seen in the brush head shown in FIG. 2B. However, it can be anticipated that the retention element 50 may be completely embedded in the flexible matrix 30' or omitted, such as in FIG. 2A. In an alternative arrangement, the flexible matrix 30' may not completely encompass the retention element 50 as shown in FIG. 3D, and instead the flexible matrix 30' could just be provided between the proximal end portions 26 of the bristle tufts 21 and the platen 24.

Figure 3E:
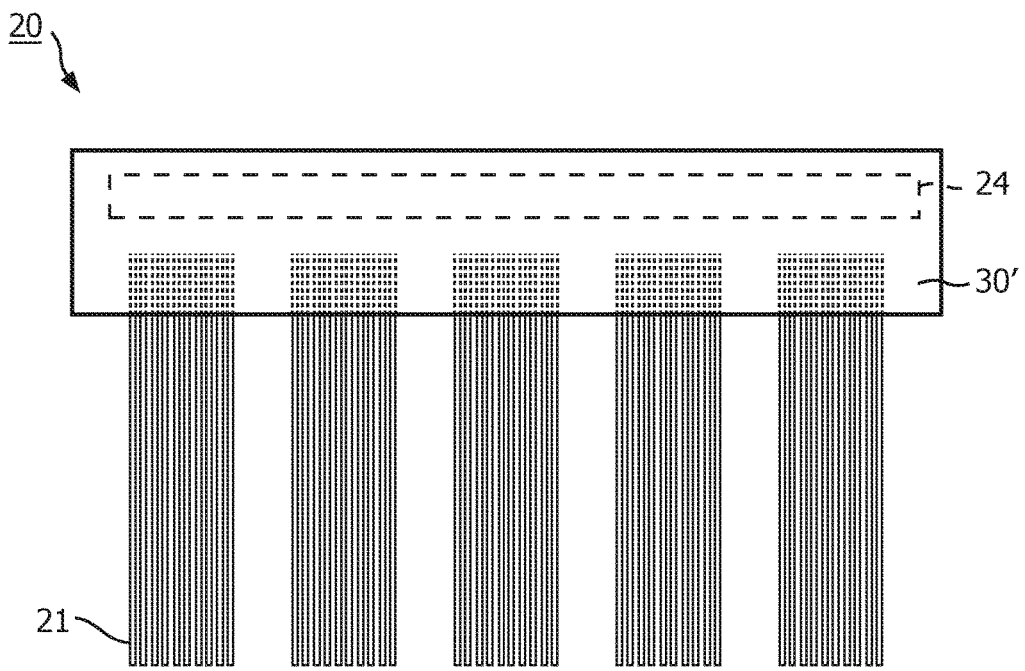
FIG. 3E is a schematic representation of a portion of a brush head assembly in accordance with an embodiment.

FIG. 3E shows another embodiment of a head portion 20 designed to improve retention of bristles and bristle tufts 21 within the flexible matrix 30'. The embodiment in FIG. 3E corresponds to that shown in FIG. 3A, except that the shear-thickening material (flexible matrix 30') completely encompasses the platen 24. Thus, the flexible matrix 30' can be molded over or around the hard platen 24 and around the proximal ends 23 of the bristle tufts 21 to retain the bristle tufts 21 in the head portion 20.

Figure 4:
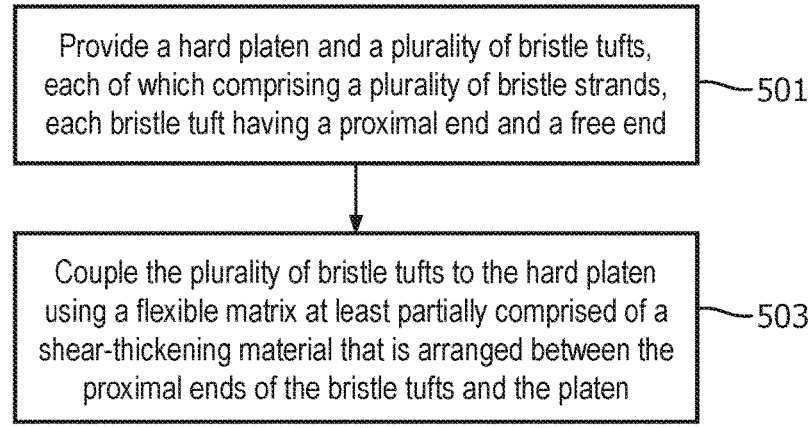
FIG. 4 is a flow chart illustrating a method of manufacturing a brush head assembly in accordance with an embodiment.

The flow chart in FIG. 4 shows a method of manufacturing a brush head assembly 100 for use with a personal care appliance 10 according to the embodiments shown in FIGS. 3A-3E. In a first step, step 501, a hard platen 24 and a plurality of bristle tufts 21 are provided. The bristle tufts 21 comprise a plurality of bristle strands, and the tufts have a proximal end 23 and a free end 25. The bristle tufts 21 and platen 24 can be formed or manufactured according to any conventional technique.

In step 503, the plurality of bristle tufts 21 are coupled to the hard platen 24 using a flexible matrix 30'. The flexible matrix 30' is at least partially comprised of a shear-thickening material, and the flexible matrix 30' is arranged such that there is shear-thickening material between the proximal ends 23 of the plurality of bristle tufts 21 and the hard platen 24.

Providing shear-thickening material between the proximal ends 23 of the plurality of bristle tufts 21 and the hard platen 24 enables vertical movement of the bristle tufts 21 relative to the platen 24.

In some embodiments, step 501 can comprise forming the proximal ends of the bristle strands in each bristle tuft into a proximal end portion 26.

In some embodiments, the method can further comprise using at least one retention element 50 to secure the bristle tufts 21 in the flexible matrix 30'. The retention element can be at least partially encompassed by the flexible matrix 30'.

In some embodiments, step 503 can comprise bonding the flexible matrix 30' to at least a portion of the hard platen 24. In some embodiments, step 503 can also or alternatively comprise bonding the flexible matrix 30' to the proximal end 23 of the bristle tufts 21.

In other arrangements of the present invention, which are described with reference to FIGS. 5A-5E, FIG. 6 and FIGS. 7A-7B, a brush head assembly 100 has bristle tufts retained within or interconnected by a sandwich of flexible material between two layers of stiffer material. In particular, the bristle tufts 21 can be retained within retention elements 250, and the retention elements 250 can be coupled or fixed together using a sandwich made of two layers of stiff or stiffer material with a flexible material between the layers of stiff material to form part of the head portion 20 of the brush head assembly 100. The flexible material can be an elastomeric resin, or some other soft or flexible material, such as an elastomer or polymer, that allows for some deformation. In some embodiments, the flexible matrix 30" can be a foam, or other air- or fluid-filled material. In some embodiments, the flexible matrix 30" can be an air or fluid chamber.

In operation, motion of one bristle tuft (for example caused by motion of a drive shaft of a personal care appliance) is imparted to other bristle tufts via the sandwich assembly, with the soft layer deforming and the stiff layers imparting lateral force to the bristle tufts. The sandwich assembly also allows vertical movement of the bristle tufts (i.e. movement along the axis of the bristle tufts) to enabled the brush head to conform to tooth surfaces better, providing a better cleaning experience.

Figure 5A:
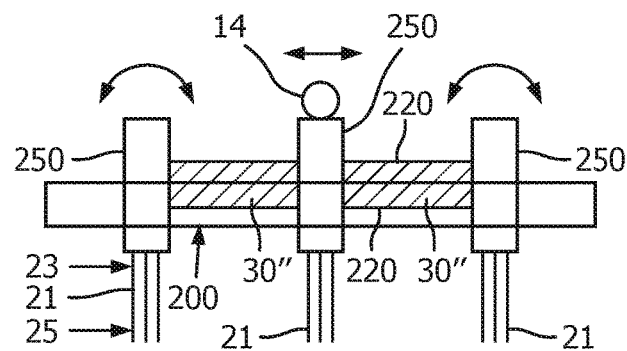
FIG. 5A is a schematic representation of a sandwich assembly of the present invention.

Referring to FIG. 5A, the core portion of a brush head assembly 100 of the subsequent embodiments of the present invention is shown. A sandwich assembly 200 is shown. The sandwich assembly 200 consists of a flexible matrix 30" positioned between two layers 220 of stiff or stiffer material. The layers 220 could be formed from plastic, for example any type of plastic typically used in a brush head assembly, such as polypropylene, or any other rigid or stiff material, e.g. metal. The flexible matrix 30" enables the two layers 220 of stiffer material to move with respect to each other, and in particular the sandwich assembly 200 is such that the two layers 220 can move in opposite directions.

The brush head assembly 100 includes a plurality of bristle tufts 21, each of which comprises a plurality of bristle strands. According to an embodiment, the bristle tufts are composed of nylon, or another suitable material. Each bristle tuft includes a proximal end 23 and a free end 25. A respective bristle tuft retention element 250 is used to hold the proximal end 23 of a bristle tuft 21. The retention elements 250 can be formed from any suitable material, for example a plastic, such as polypropylene. The bristle tuft retention elements 250 are interconnected with each other using the sandwich assembly 200. In particular, the layers 220 are connected to the bristle tuft retention elements 250. For example the edge of the layers 220 can be bonded to the tuft retention elements 250. The flexible matrix 30" can be an elastomeric resin or some other soft or flexible material such as a polymer, that allows for some deformation when force or motion is applied. The flexible matrix 30" is sandwiched between two layers 220 of a stiffer material. The stiffer material needs to be thick enough, and of a stiff enough material to provide some structure and rigidity to the brush head portion 20, and also to impart lateral force (i.e. force that is used to sweep the bristles over the teeth) to the bristle tufts 21 in the bristle tuft retention element 250 from the drive shaft 14 when the brush head is being operated. FIG. 5A shows drive shaft 14 connected to, or otherwise in contact with a particular bristle tuft retention element 250, and also shows the direction of oscillation of the drive shaft 14. This oscillatory motion will be transferred from the particular bristle tuft retention element 250 to the other bristle tuft retention elements 250 via the sandwich assemblies 200 connecting the bristle tuft retention elements 250. It will be appreciated that, although shown in FIG. 5A, the drive shaft 14 is not part of the brush head assembly 100. It will also be appreciated that FIG. 5A only illustrates a single row of bristle tufts 21, and a brush head assembly 100 may comprise several rows of bristle tufts 21, with the drive shaft 14 being coupled or connected to a single tuft retention element 250 in each row.

Figures 5B, 5C:
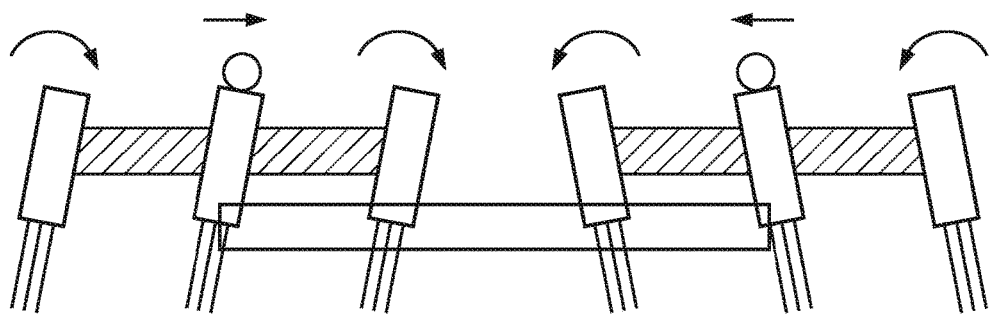
FIGS. 5B-E illustrate the operation of the sandwich assembly of FIG. 5A.
Figures 5D, 5E:
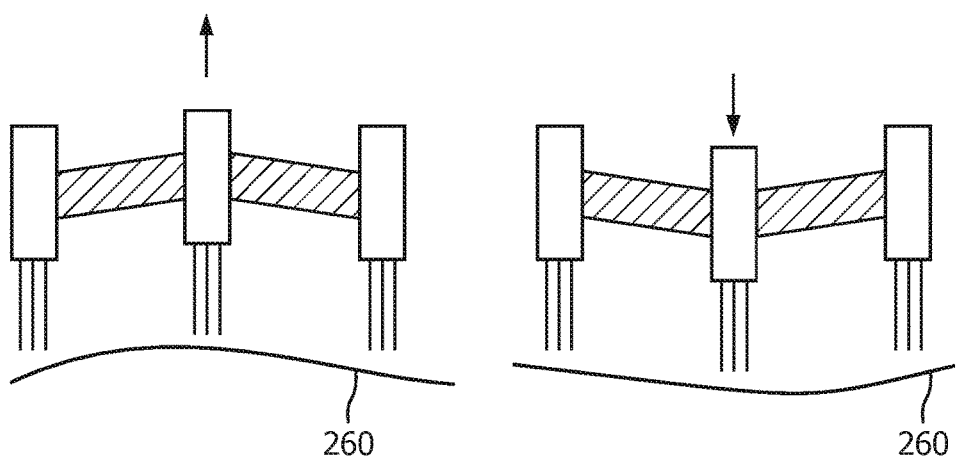

FIGS. 5B-5E illustrate the operation of a brush head 100 that is constructed according to the arrangement in FIG. 5A. FIGS. 5B and 5C illustrate how the oscillatory motion of a particular bristle tuft retention element 250 caused by drive shaft 14 is transmitted to the other bristle tuft retention elements 250 via the sandwich assemblies 200 since the flexible matrix 30" enables the two layers 220 of stiffer material to move with respect to each other. FIGS. 5D and 5E illustrate that the sandwich assembly 200 connections between the bristle tuft retention elements 250 allow the bristle tuft retention elements 250 (and hence the bristle tufts 21 carried therein) to move vertically with respect to each other in order to follow the contours or topology of a surface 260 (e.g. a tooth or gum). The flexible matrix 30" provides a suitable level of resistance to vertical forces that occur as the bristles are moved across the surface of a tooth or gum.

Thus, while conventional brush heads have a comparatively simple construction, the key advantages of the illustrated embodiments derive from the non-uniform mechanical construction of the sandwich assembly 200 that gives very different stiffness in different modes of motion. As described above the sandwich layer 200 is rigid to transmitting the oscillating twisting motion between tufts 21, but is very soft to deformation in the direction of the bristles, which are normally roughly perpendicular to the teeth. In the embodiments described below the arrangement in FIG. 5 is combined with other features to provide a more regulated down force to each tuft 21, than can be provided by existing brush heads. This, then results in the tufts 21 moving until in contact with the tooth surface, ensuring superior tuft contact, and therefore cleaning performance.

Thus, the use of a sandwich assembly 200 as described provides a brush head structure that maintains high lateral forces on the bristles, while providing a low force for conformation. This combination results in superior overall cleaning performance. In addition, this can change the factors that are used to determine bristle length (i.e. the improved cleaning performance can allow for shorter bristles). Thus, it can provide more compact head geometry, giving better access to difficult areas.

Figure 6:
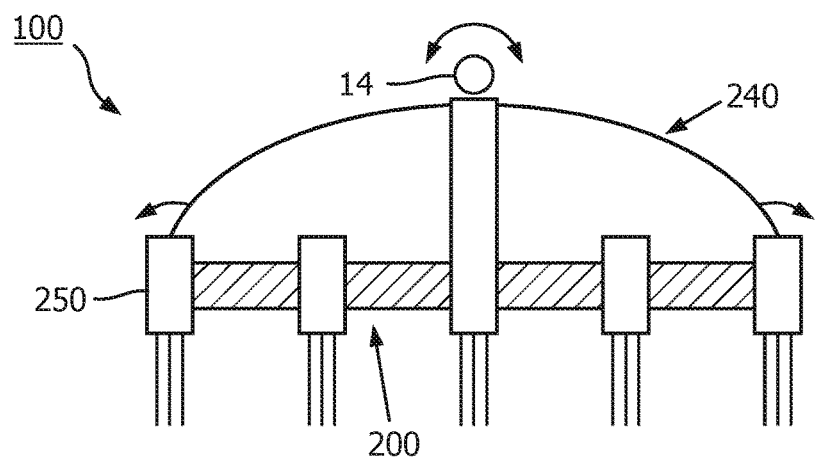
FIG. 6 is a schematic representation of a portion of a brush head assembly in accordance with an embodiment.

A further embodiment is shown in FIG. 6. Although not shown in FIG. 6, the brush head 100 includes a neck 40 which can be coupled to any tooth brush actuator and drive shaft 14 (which is shown) made or suitable for oral care devices now known or to be developed. In this embodiment the brush head 100 also includes a backing material 240 that can be used to encapsulate and hold the sandwich assembly 200 and the neck 40 together. The backing material 240 is provided to help direct force from the drive shaft 14 via the neck 40 down to the bristle tufts 21. The backing material 240 is also provided to modulate the force exerted by the bristle strands in the vertical direction.

As described above with reference to FIGS. 5A-5E, in operation, the drive shaft 14, and the attached neck 40 pivot back and forth about a center axis. A central line of bristle tufts 21 is in line with the neck 40 and drive shaft 14, and these bristle tufts 21 are driven by the motion of the drive shaft 14. The other bristle tufts 21 in the brush head 100 are indirectly powered by the motion of the drive shaft through the coupling of the sandwich assembly 200. The drive shaft motion is imparted to the bristle tuft retention elements 250 by the sandwich assembly 200, and thus the bristle tufts 21 in those bristle tuft retention elements 250, by means of the flexible material 30" in the sandwich assembly 200 allowing the relative movement of the layers 220 of stiff material. Because of the flexible material 30" the sandwich itself can move and twist, and the bristle tuft retention elements 250 incorporated into the sandwich assembly 200 impart the motion to the bristle tufts 21. In some embodiments, the backing material 240 helps to provide additional shape and structure to the brush head 100, and helps direct the motion of the drive shaft 14 down to the bristle retention elements 250 and the sandwich assembly 200, rather than the motion being dissipated in various directions. The backing material 240 is generally a soft, flexible material, such as an elastomer or polymer, that can adapt to twisting motion of the brush head, and can even be a chamber filled with air or another gas or a suitable liquid. The mechanical parameters (e.g. stiffness, density) of the backing material 240 is chosen so that the backing material 240 does not transmit the drive frequency to the sandwich assembly 200 efficiently, preventing the brush head assembly 100 rotating as a semi-rigid body. Instead, it provides a down force on each tuft 21 to enable the tuft 21 to gain good contact, which can respond to the motion of the brush head over the oral cavity, at timescales of typically a few Hz. Meanwhile, the sandwich assembly 200 transmits the high frequency bristle motion efficiently to each tuft 21, ensuring the bristles move and can be effective at removing plaque. When used with a soft backing material 240, the flexible matrix 30" can be a material that has a high density to provide the brush head assembly 100 with higher inertia. For example it may be preferred for the flexible matrix 30" to be a soft elastic solid, such as a soft silicone elastomer, rather than a polymer foam or sponge, as the higher density helps make the response time of the sandwich assembly 200/backing material 240 combination be in the desired frequency range. The bristle tuft retention element 250 can be cups, retention rings, sleeves, anchors, or the like, or an interconnected web of one or more such mechanisms. If a web is used, it can even form a part of the layer 220 of stiffer material that is part of the sandwich 200.

The flexible matrix 30" in the sandwich assembly 200 may be generally flat, as shown in the figures, but in some embodiments the flexible matrix 30" may be curved so that when the bristles are loaded on to the tooth surfaces the force distribution is reasonably uniform.

Figure 7A:
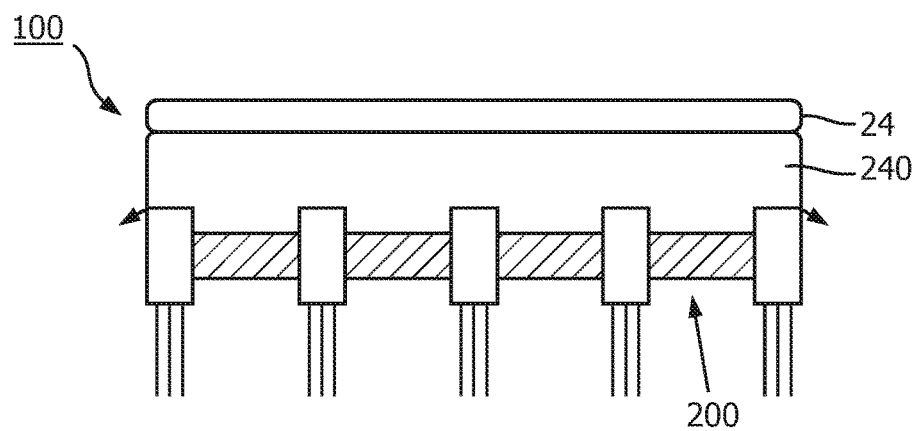
FIG. 7A is a schematic representation of a portion of a brush head assembly in accordance with an embodiment.

FIG. 7A shows another arrangement of a brush head 100 of the present invention. The brush head 100 has a sandwich assembly 200 as described above which consists of a flexible matrix 30" positioned between two layers 220 of stiffer material. In this embodiment the brush head 100 also includes a platen 24, which is made of a rigid material to provide further structure and rigidity to the brush head 100. The brush head 100 also includes a backing material 240 that is used to encapsulate and hold together the sandwich assembly 200, at least a portion of the platen 24, and the neck 40 (not shown in FIG. 7A). In operation, the brush head 100 works as described with respect to the brush head 100 of FIGS. 5 and 6. The platen 24 helps to provide additional structure to the brush head 100, and helps direct the motion of the drive shaft (which is coupled to a tuft retention element 250) down to the sandwich assembly 200 and the other bristle retention elements 250, rather than the motion being dissipated in various directions (although it will be appreciated that the platen 24 does not move with the motion of the drive shaft). In this embodiment, the backing material 240 can be a soft elastomer or a soft walled air or fluid chamber that connects the platen 24 to the sandwich assembly 200 and the tufts 21. This construction, especially with an air or fluid chamber, allows a completely uniform normal force distribution on the tufts 21. In some embodiments the force distribution can be monitored by a (force) pressure sensor that can be located in the brush head 100, or located in the handle 11 and connected to the backing material 240 by an air channel.

Figure 7B:
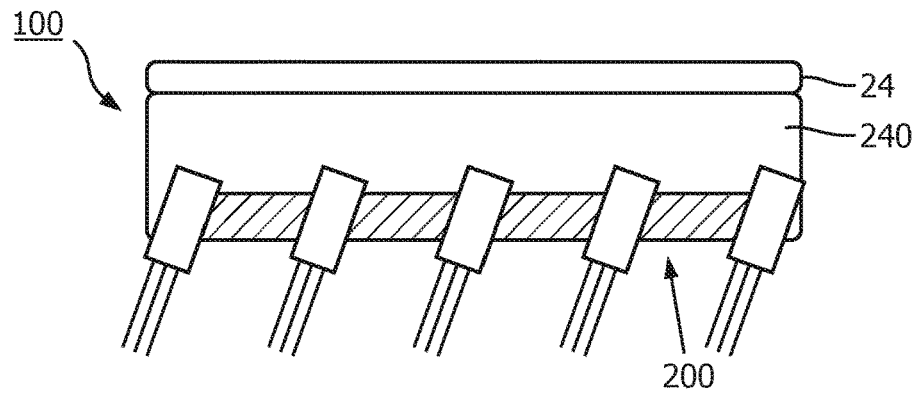
FIG. 7B is a schematic representation of a portion of a brush head assembly in accordance with an embodiment.

FIG. 7B shows another arrangement of a brush head 100 of the present invention. This brush head corresponds to the arrangement shown in FIG. 7A, except that, as can be seen, the drive shaft 14 has been rotated with respect to the platen 24, which tilts the bristle tufts 21 (but not the complete brush head assembly 100) via the sandwich assembly 200. Bristle tufts 21 that are at an angle with respect to the tooth (and that oscillate around that tilted angle) may have increased contact with the tooth surface, resulting in improved contact and better cleaning. Thus, angling the drive shaft 14 can be used to tilt the bristles to an optimum direction towards the gum line, and, in some embodiments, could be automatically performed by the motor controller 12 in the toothbrush handle 11, for example in response to measurements by an angle sensor (e.g. an accelerometer), to determine the ideal direction and amount of tilt of the drive shaft 14.

In a conventional brush head, when the bristles are tilted towards the gum line, the whole head rotates, and so many of the bristles are out of contact with the tooth surfaces that need cleaning. In contrast, with the brush head assembly 100 according to this embodiment, the bristles can be tilted, but all remain in contact with surfaces that need to be cleaned. Thus cleaning efficiency can be significantly improved over existing brush head designs.

Figure 8A:
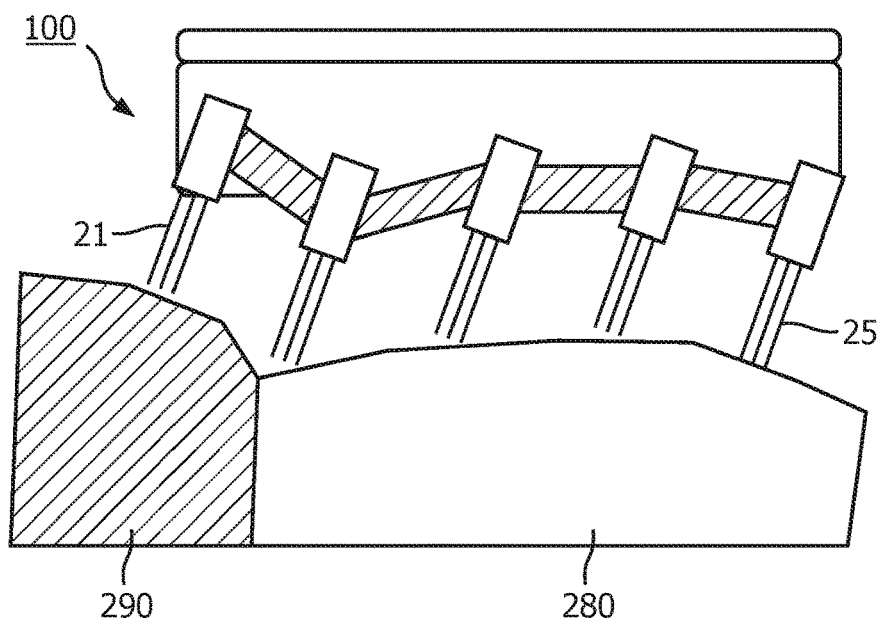
FIG. 8A is a schematic representation of one arrangement of a brush head assembly of the present invention being applied to the teeth and gums in operation.
Figure 8B:
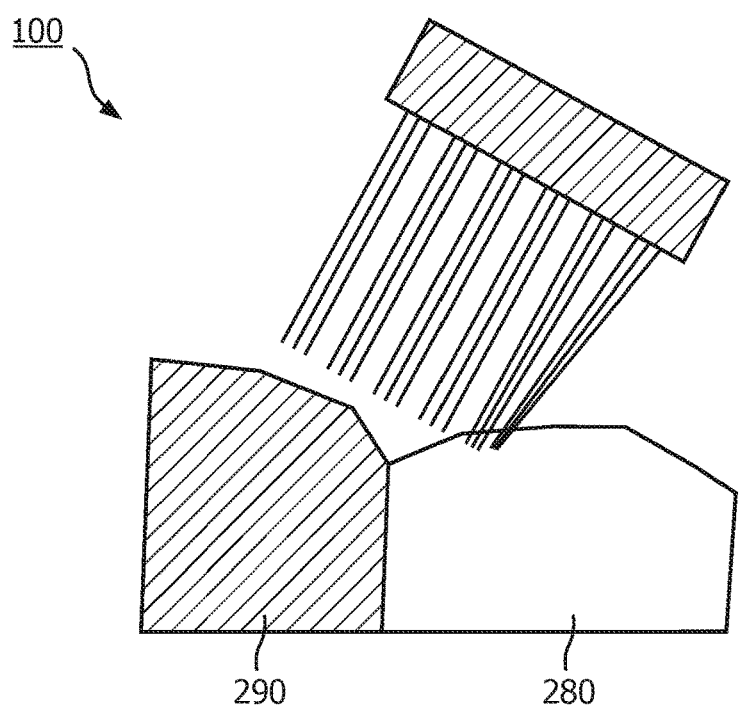
FIG. 8B is a schematic representation of a brush head assembly of the prior art being applied to the teeth and gums in operation.

The above advantages can be seen more clearly in FIGS. 8A and 8B. FIG. 8A shows a brush head assembly 100 of the present invention with the sandwich layer 200 operating as intended, and flexing the bristle tufts 21 of the brush head 100 in response to the bristle tufts 21 coming in contact with the various tooth surfaces 280 and the gum 290. As can be seen in FIG. 8A, the sandwich layer 200 flexes as intended, such that the various bristle tufts 21 flex and shift with the motion of the drive shaft 14, but also in response to the upward pressure applied to the free end 25 of the bristles by the tooth 280, which helps keep the bristle tips at an optimum angle with the surface being cleaned for better contact and therefore better cleaning.

In contrast, FIG. 8B shows a brush head of the prior art, where the ends of the bristle tufts bend in when in contact with the surface of the tooth 280, but the bristle tips bend away from, rather than make contact with, the tooth surface and the rigid platen and the fixed bristle positions prevent many of the bristles from coming into a good contact force range (some too high, some too low) for efficient cleaning.

Therefore, it can be appreciated, that the material properties of the different components of the brush head 100 of the present invention interact together to provide sufficient structure and rigidity to the brush head 100, while providing sufficient flexibility to enable movement of the different bristle tufts 21 in response to the motion of the drive shaft of the tooth brush and counter-pressure of the surface being brushed.

Figure 9:
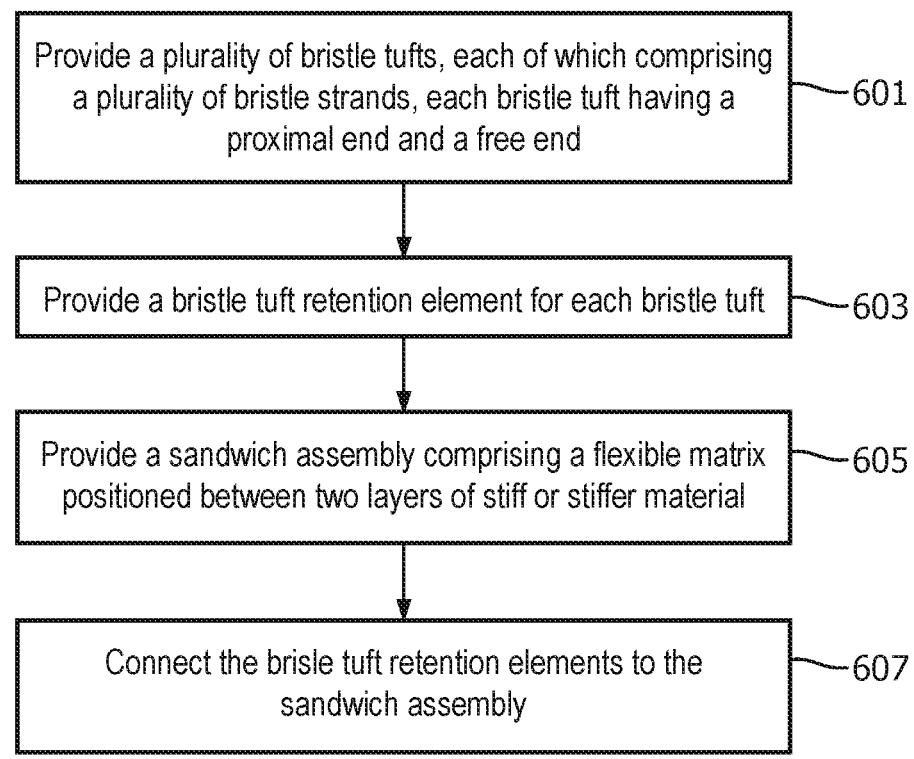
FIG. 9 is a flow chart illustrating a method of manufacturing a brush head assembly in accordance with an embodiment.

The flow chart in FIG. 9 shows a method of manufacturing a brush head assembly 100 for use with a personal care appliance 10 according to the embodiments shown in FIGS. 5A-5E. In a first step, step 601, a plurality of bristle tufts 21, each of which comprising a plurality of bristle strands, are provided. Each bristle tuft 21 has a proximal end 23 and a free end 25. The bristle tufts 21 can be formed or manufactured according to any conventional technique.

In step 603, a bristle tuft retention element 250 is provided for each bristle tuft 21. The bristle tuft retention element 250 holds or retains the bristle tuft 21. The bristle tuft retention elements 250 can be formed or manufactured according to any conventional technique.

In step 605, a sandwich assembly 200 comprising a flexible matrix 30″ positioned between two layers 220 of stiff or stiffer material is provided.

Finally, in step 607, the bristle tuft retention elements 250 are connected to the sandwich assembly 200, so that oscillatory motion of one bristle tuft retention element 250 (for example by a drive shaft 14 of a personal care appliance 10) is imparted to the other bristle tuft retention elements 250 via the sandwich assembly 200.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously used in a power toothbrush for use in dental healthcare applications. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device or apparatus claim enumerating several means, several of these means may be embodied by one and the same item of hardware. The mere fact that certain measures are recited in mutually different dependent claims does not indicate that a combination of these measures cannot be used to an advantage.

Statements relating to some particular embodiments are set out below

1. A brush head assembly (100) comprising:
    a hard platen (24);
    a plurality of bristle tufts (21), each of which comprises a plurality of bristle strands having a proximal end (23) and a free end (25); and
    a flexible matrix (30′) at least partially comprised of a shear-thickening fluid bonded to and encompassing at least a portion of the hard platen, and the proximal end of the bristle tufts.
2. The brush head assembly of statement 1, wherein the proximal end (23) of the bristle tufts (21) is formed into a proximal end portion (26) that is bonded to the flexible matrix (30′).
3. The brush head assembly of statement 1, wherein the proximal end of the bristle tufts is attached to the hard platen (24).
4. The brush head assembly of statement 1 or statement 2 further comprising at least one retention element (50) to secure the bristle tufts (21) in the flexible matrix (30'), the retention element at least partially encompassed in the flexible matrix (30').

5. A brush head assembly (100) comprising:

A neck (40) for coupling to a drive shaft of a toothbrush;

A sandwich assembly (200) comprising a flexible matrix (30") positioned between two layers of stiffer material (220), a plurality of bristle tufts (21), each of which comprises a plurality of bristle strands having a proximal end (23) and a free end (25), a bristle tuft retention element (250) for securing the proximal end of the bristle tufts in the sandwich assembly; and a backing material (240) that at least partially encompasses the neck and the sandwich assembly.

6. The brush head assembly of statement 5 further comprising a hard platen (24).

7. The brush head assembly of statement 6 wherein the hard platen is at least partially encompassed by the backing material (240).

8. The brush head assembly of statement 5, wherein the flexible matrix (30") is at least partially composed of a shear-thickening material.

9. The brush head assembly of statement 6, wherein the hard platen (24) is at an angle with respect to the neck (40) and sandwich assembly (200).

10. The brush head assembly of statement 5 wherein the backing material encompasses a chamber filled with a gas or liquid.

What is claimed is:

1. A brush head assembly comprising:
a sandwich assembly comprising a flexible matrix positioned between two layers of stiff or stiffer material,
a plurality of bristle tufts, each of which comprises a plurality of bristle strands, each bristle tuft having a proximal end and a free end,
a bristle tuft retention element for each bristle tuft, the bristle tuft retention elements connecting the proximal end of the bristle tufts to the sandwich assembly.

2. The brush head assembly of claim 1, wherein the sandwich assembly is such that the two layers of stiff or stiffer material are capable of moving with respect to each other in order to transmit an oscillating motion of a first retention element to a second retention element.

3. The brush head assembly of claim 1, wherein the sandwich assembly is such that the two layers of stiff or stiffer material are capable of moving with respect to each other in response to an applied force in order to change a vertical position of a first bristle tuft with respect to a second bristle tuft.

4. The brush head assembly of claim 1, further comprising:
a backing material that at least partially encompasses one side of the sandwich assembly.

5. The brush head assembly of claim 4, wherein the backing material is provided to modulate a force exerted by the bristle strands in a vertical direction.

6. The brush head assembly of claim 4 further comprising a hard platen that is connected to the backing material.

7. The brush head assembly of claim 6 wherein the hard platen is at least partially encompassed by the backing material.

8. The brush head assembly of claim 4, wherein the backing material is a chamber filled with a gas or liquid.

9. The brush head assembly of claim 1, wherein the flexible matrix is composed of an elastomer or a polymer.

10. The brush head assembly of claim 1, wherein the flexible matrix is a chamber filled with a gas or liquid.

11. The brush head assembly of claim 1, wherein the flexible matrix is composed of a high density material.

12. The brush head assembly of claim 1, wherein at least one of the bristle tuft retention elements is configured to receive an oscillating motion from a drive shaft of a personal care appliance.

13. A personal care appliance comprising:
a handle including a drive train and a drive shaft;
a motor controller for controlling operation of the drive train to produce a mechanical stimulus; and
a brush head assembly as claimed in claim 1.

14. A method of manufacturing a brush head assembly for use with a personal care appliance, the method comprising:
providing a plurality of bristle tufts, each of which comprising a plurality of bristle strands, each bristle tuft having a proximal end and a free end;
providing a bristle tuft retention element for each bristle tuft;
providing a sandwich assembly comprising a flexible matrix positioned between two layers of stiff or stiffer material; and
connecting the bristle tuft retention elements to the sandwich assembly.

* * * * *